Dec. 8, 1959 R. G. JELLY Plant Pat. 1,888
ROSE PLANT
Filed March 26, 1959
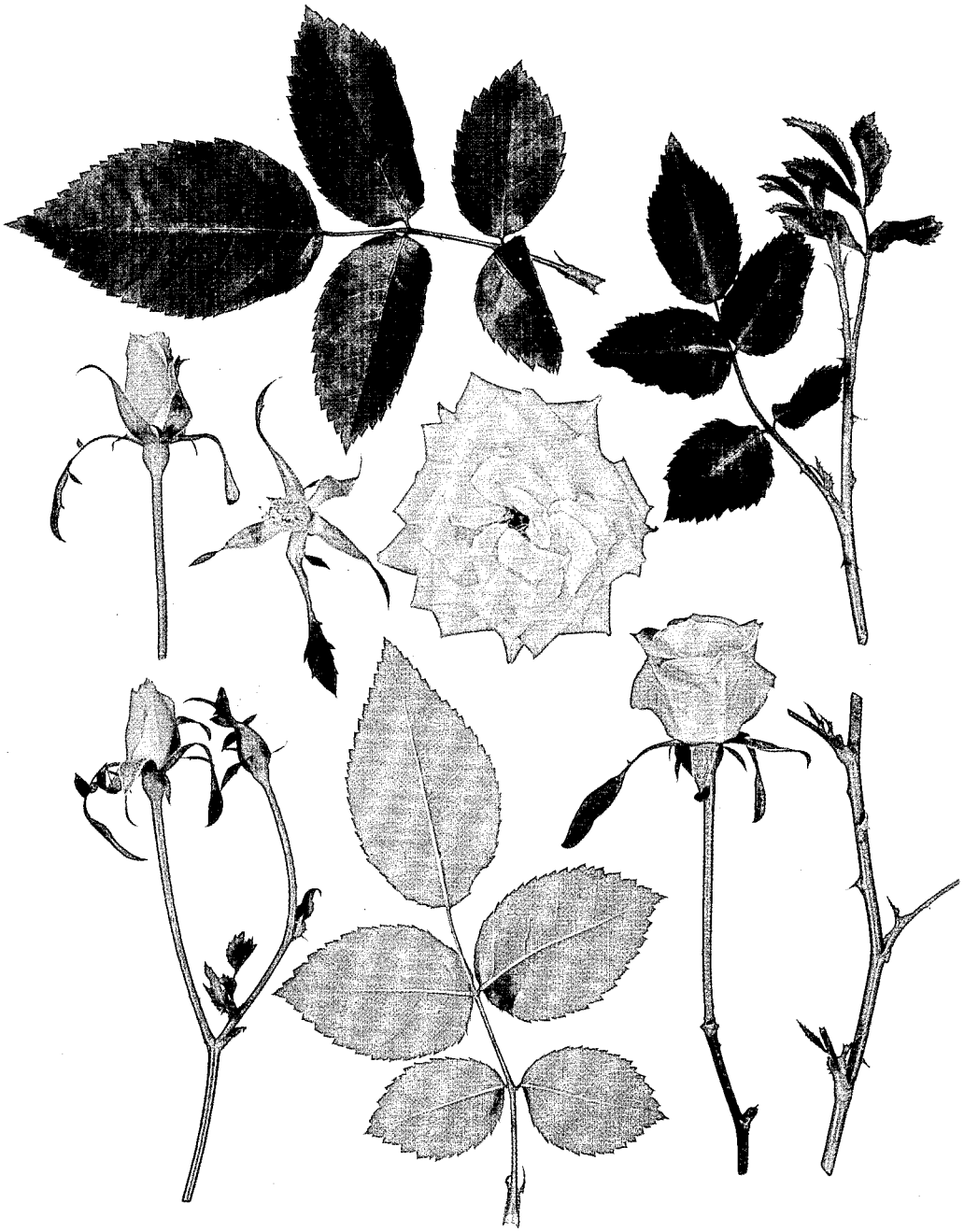
INVENTOR
R. G. Jelly
BY Robb & Robb
ATTORNEYS United States Patent Office Plant Pat. 1,888
Patented Dec. 8, 1959

1,888

ROSE PLANT

Robert G. Jelly, Richmond, Ind., assignor to E. G. Hill Co., Inc., Richmond, Ind., a corporation of Indiana Application March 26, 1959, Serial No. 802,275

1 Claim. (Cl. 47—61)

The present invention relates to a new and distinct variety of rose plant of the polyantha class, which was originated by me by crossing the variety "Garnette" (unpatented) with an unnamed and unpatented seedling of "Garnette."

The primary objective of this breeding was to produce a new rose variety characterized by a high flower productivity, flowers of floribunda size capable of being grown for commercial cut flower production with a minimum of disbudding to cause the flowers to be borne on single stems, and good keeping qualities of the flowers when used for cut flowers. These characteristics were fully attained, along with other desirable improvements, as evidenced by the following unique combination of characteristics which are outstanding in the new variety and which distinguish it from its parents, as well as from all other varieties of which I am aware:

(1) A very free habit of growth;
(2) Excellent flower production;
(3) A habit of bearing flowers on stems of adequate length for cut flowers;
(4) Good keeping qualities of the flowers; and
(5) An attractive medium pink general color tonality of the blooms.

As compared with its seed parent, "Garnette," the new variety is a freer grower and much more productive in its flowering habit, while the color of the flowers is pink, instead of red.

In comparison with its pollen parent, the new variety is also much more productive in its flowering habit, although the flowering stems are somewhat shorter than those of this parent, and the color of the blooms is pink, as distinguished from the red flower color of this parent.

Asexual reproduction of the new variety by grafting, as performed by me at Richmond, Indiana, shows that the foregoing characteristics and distinctions come true to form and are established and transmitted through succeeding propagations.

The accompanying drawing shows typical specimens of the vegetative growth and flowers of my new variety in different stages of development, and as depicted in color as nearly true as it is reasonably possible to make the same in a color illustration of this character.

The following is a detailed description of my new variety, with color terminology in accordance with Robert S. Wilson's Horticultural Colour Chart (hereinafter abbreviated as "Wilson"), Koster's Color Guide (hereinafter abbreviated as "Koster") and Ridgway's Color Standards and Nomenclature (hereinafter abbreviated as "Ridgway"), as indicated, except where general color terms of ordinary dictionary significance are obvious:

Type: Seedling; greenhouse; for cut flower production.
Class: Polyantha.
Breeding: Seedling.
*Seed parent.*—"Garnette."
*Pollen parent.*—An unnamed seedling of "Garnette."

Propagation: Holds its distinguishing characteristics through succeeding propagations by grafting.

*Flower*

Locality where grown and observed: Richmond, Indiana.
Flowers borne: From 1 to 3 to stem; can be disbudded and grown commercially one to a stem; on moderately strong, short stems.
Quantity of bloom: Abundant, in greenhouse.
Continuity: Continuous, in greenhouse.
Fragrance: Slight, in greenhouse. Nature—sweetbriar.
Bud:
*Peduncle.*—Medium length; small diameter; strong; erect. Bark—slightly rough; color—Scheeles Green, Plate 860 (Wilson). Thorns—none. Prickles—numerous; color—Dresden Yellow, Plate 64/3 (Wilson). Hairs—none.
*Before calyx breaks.*—Size—small. Form—short pointed; with a conspicuous neck; with foliaceous appendages on the surface of the bud; with slender, slightly cut, bristle-like foliaceous parts extending beyond the tip of the bud equal to from ¼ to ¾ or more of its length. Color—Scheeles Green, Plate 860/2 (Wilson).
*As calyx breaks.*—Color—Magenta Rose, Plate 027/1 (Wilson).
*As first petal opens.*—Size—small. Form—short pointed. Color: outside—Phlox Pink, Plate 625/1 (Wilson); inside—Solferino Purple, Plate 26/1 (Wilson).
*Opening.*—Opens up well in greenhouse; is affected by hot, dry weather by being slightly smaller in bud size.
Bloom:
*Size (when fully open).*—Small; from 2½ inches to 3 inches.
*Petalage.*—Double (more petals, but the stamens not hidden); from 25 to 34 petals; arranged regularly.
*Form.*—High-centered at first, but becoming from flat to high-centered; petals being at first tightly rolled outward, but becoming later at maturity from flat to slightly cupped.
Petals:
*Texture.*—Moderately thick and soft. Inside—satiny. Outside—non-glossy, but smooth.
*Shape.*—Outer—from oval to obovate, with apex slightly mucronate, and with from 1 to several small apical points. Intermediate—from oval to obovate, with apex mucronate, and with 1 small apical point. Inner—from oval to slightly obovate, with apex having from 1 to 3 small notches.

This description of a newly opened flower was made from a rose grown in a greenhouse in the month of October at Richmond, Indiana:

*Color.*—Outer petal: outside surface—Rhodamine Pink, Plate 527 (Wilson), with base Sea Foam Yellow, Plate XXXI (Ridgway); inside surface—Magenta, Plate 27/2 (Wilson), with base Sea Foam Yellow, Plate XXXI (Ridgway). Intermediate petal: outside surface—Magenta, Plate 27/2 (Wilson), with base between white and Marguerite Yellow, Plate XXX (Ridgway); inside surface—Phlox Pink, Plate 625/1 (Wilson), with base Marguerite Yellow, Plate XXX (Ridgway). Inner petal: outside surface—Magenta, Plate 27/2 (Wilson), with base almost white; inside surface—Fuchsine Pink, Plate 627/1 (Wilson), with base almost white.

During the short day period of the year (from late November to early February) the petals are edged with a thin, almost white border which is not apparent during all of the year.

This description was made from a rose that was open for 3 days in a greenhouse in the month of October at Richmond, Indiana:

*Color.*—Outer petal: outside surface—Fuchsine Pink, Plate 627/2 (Wilson), with base lighter than Sea Foam Yellow, Plate XXX (Ridgway); inside surface—Tyrian Rose, Plate 24/2 (Wilson), with base lighter than Marguerite Yellow, Plate XXX (Ridgway). Intermediate petal: outside surface—Fuchsine Pink, Plate 627/2 (Wilson), with base almost white; inside surface—Solferino Purple, Plate 26/2 (Wilson), with base almost white. Inner petal: outside surface—Phlox Pink, Plate 625/2 (Wilson), with base almost white; inside surface—Solferino Purple, Plate 26/2 (Wilson), with base almost white.

*General color effect.*—Newly opened flower—Phlox Pink, Plate 625/1 (Wilson). 3-days open—Rhodamine Pink, Plate 527 (Wilson).

*Behavior.*—Persist in greenhouse; affected by hot weather by fading to Pale Amaranth Pink, Plate XII (Ridgway).

*Flower longevity.*—Cut roses grown in greenhouse and kept at living-room temperatures—6 or 7 days in October.

*Plant*

Foliage:

*Leaves.*—Compound of from 3 to 5 leaflets; normal abundance; medium size; moderately heavy.

*Leaflets.*—Shape—from oval to elliptical, with apex cuspidate. Base—from obtuse to slightly cordate. Margin—simply serrate.

*Color.*—Mature: upper surface—Empire Green, Plate XXXII (Ridgway); under surface—slightly lighter than Cedar Green, Plate 80 (Koster). Young: upper surface—Warm Blackish Brown, Plate XXXIX (Ridgway); under surface—Dark Violet, Plate 58 (Koster).

*Rachis (the supporting stem of the compound leaf).*—Medium caliper. Upper side—grooved; slightly prickly, but otherwise almost smooth. Under side—thorny (small and few).

*Stipules.*—Moderately short; narrow; with moderately short points turning out at an angle of less than 45°.

Growth (in greenhouse):

*Habit.*—Upright; much-branched.

*Growth.*—Free; vigorous.

*Canes.*—Small.

*Main stems.*—Color—Forest Green, Plate XVII (Ridgway). Thorns—from few to several; medium length; hooked slightly downward; narrow; color—Verona Brown, Plate XXIX (Ridgway). Prickles—none. Hairs—none.

*Branches.*—Color—Spinach Green, Plate V (Ridgway). Thorns—few; medium length; hooked slightly downward; with narrow base; color—Chrysolite Green, Plate XXXI (Ridgway) at tip, shading to Dark Olive Buff at base, Plate XL (Ridgway). Prickles—very few; color—Light Green-Yellow, Plate V (Ridgway). Hairs—none.

*Reproductive organs*

Stamens: Medium number; arranged regularly about pistils; tucked in calyx.

Filaments: Medium length; most with anthers. Color—Deep Sea Foam Green, Plate XXXI (Ridgway).

Anthers: From medium size to small; all open at once. Color—Marguerite Yellow, Plate XXX (Ridgway).

Pollen: Moderate abundance. Color—Chamois, Plate XXX (Ridgway).

Pistils: Medium number.

Styles: Uneven; medium length; moderately thin; bunched; columnar. Color—Primrose Yellow, Plate XXX (Ridgway).

Stigma: Color—Reed Yellow, Plate XXX (Ridgway).

Ovaries: All enclosed in calyx.

Hips: Short; globular; with inconspicuous neck; gourd-shaped; moderately smooth; walls thin. Color—Persimmon Orange, Plate 7/0 (Wilson).

Sepals: Permanent; moderately short.

Seeds: Few; small.

I claim:

A new and distinct variety of rose plant of the polyantha class, substantially as herein shown and described, characterized particularly as to novelty by the unique combination of a very free habit of growth, excellent flower production, a habit of bearing flowers on stems of adequate length for cut flowers, good keeping qualities of the flowers, and an attractive medium pink general color tonality of the blooms.

No references cited.